US010405890B2

(12) United States Patent
Ratron et al.

(10) Patent No.: US 10,405,890 B2
(45) Date of Patent: Sep. 10, 2019

(54) HELICAL BONE FIXATION DEVICE

(71) Applicant: Vexim S.A., Balma (FR)

(72) Inventors: Yves-Alain Ratron, Grenoble (FR); Jean-Francois Oglaza, Balma (FR)

(73) Assignee: VEXIM S.A., Balma (FR)

( * ) Notice: Subject to any disclaimer, the term of this patent is extended or adjusted under 35 U.S.C. 154(b) by 0 days.

(21) Appl. No.: 15/021,640

(22) PCT Filed: Sep. 11, 2014

(86) PCT No.: PCT/EP2014/069448
§ 371 (c)(1),
(2) Date: Mar. 11, 2016

(87) PCT Pub. No.: WO2015/036509
PCT Pub. Date: Mar. 19, 2015

(65) Prior Publication Data
US 2016/0220275 A1    Aug. 4, 2016

(30) Foreign Application Priority Data
Sep. 11, 2013 (EP) .................. 13183883

(51) Int. Cl.
*A61B 17/70* (2006.01)
*A61B 17/68* (2006.01)
(Continued)

(52) U.S. Cl.
CPC .......... *A61B 17/686* (2013.01); *A61B 17/844* (2013.01); *A61B 17/8685* (2013.01); *A61B 2017/8655* (2013.01)

(58) Field of Classification Search
CPC ........ A61B 17/686; A61B 17/70–7046; A61B 17/84–8695
See application file for complete search history.

(56) References Cited

U.S. PATENT DOCUMENTS 4,711,232 A    12/1987  Fischer et al.
5,437,674 A *  8/1995   Worcel ............... A61B 17/7225
                                                      606/308
(Continued)

FOREIGN PATENT DOCUMENTS

CN    1964673 A    5/2007
CN    102413777    4/2012
(Continued)

OTHER PUBLICATIONS

International Search Report and Written Opinion, dated Oct. 16, 2014, for International Application No. PCT/EP2014/069448.
(Continued)

*Primary Examiner* — Nicholas J Plionis
*Assistant Examiner* — Steven J Cotroneo
(74) *Attorney, Agent, or Firm* — Howard & Howard Attorneys PLLC

(57) ABSTRACT

The present invention relates to a bone fixation device (1) for securing attachment between a screw and a vertebra comprising two pedicles, comprising a hollow cavity having a longitudinal axis, a distal part (2) having itself a distal end and (7) a proximal end (8), a proximal part (3) having itself a distal end (9) and a proximal end (10) and a flange at the proximal end (10), characterized in that: —the distal part (2) comprises a deformable area (2D) comprising at least three helical slots (6); and—the distal part (2) comprises a full portion (5) located distally after said at least three helical slots (6); further characterized in that said full portion (5) cooperates with the screw such that once the screw abuts against the flange (4) of the bone fixation device (1), further screwing causes the deformation of the deformable area (2D) of the distal part (2) and the retraction of the distal end of the distal part (7) towards the proximal end of the distal (Continued)

part (8); and in that after screwing, the borders of each at least three helical slots (6) abuts against each other.

20 Claims, 5 Drawing Sheets

(51) Int. Cl.
*A61B 17/86* (2006.01)
*A61B 17/84* (2006.01)

(56) References Cited

U.S. PATENT DOCUMENTS

| | | | | |
|---|---|---|---|---|
| 5,643,321 A * | 7/1997 | McDevitt | ........... | A61B 17/0401 606/232 |
| 5,713,904 A * | 2/1998 | Errico | ................ | A61B 17/686 606/327 |
| 8,388,660 B1 * | 3/2013 | Abdou | ............... | A61B 17/8685 606/267 |
| 9,161,794 B2 * | 10/2015 | Garvey | ............. | A61B 17/8685 |
| 9,510,877 B2 * | 12/2016 | Teisen | .................. | A61B 17/68 |
| 2003/0000350 A1 * | 1/2003 | Zhao | ................. | A61B 17/8685 81/439 |
| 2005/0065526 A1 * | 3/2005 | Drew | ................... | A61B 17/686 606/63 |
| 2007/0270855 A1 * | 11/2007 | Partin | ................ | A61B 17/7225 606/279 |
| 2010/0069913 A1 * | 3/2010 | Chirico | ............. | A61B 17/1617 606/94 |
| 2012/0101530 A1 * | 4/2012 | Robling | ............. | A61B 17/7001 606/279 |
| 2016/0166291 A1 * | 6/2016 | Goel | ..................... | A61B 17/68 606/246 |

FOREIGN PATENT DOCUMENTS

| | | | |
|---|---|---|---|
| WO | WO 2002/034120 A2 | 5/2002 | |
| WO | WO 2005/096975 A2 | 10/2005 | |
| WO | WO 2010/105174 A1 | 9/2010 | |

OTHER PUBLICATIONS

Chinese Search Report for Application No. CN2014800562609 dated Dec. 15, 2017.
Extended European Search Report for Application No. EP13183883.1 dated Jan. 20, 2014.

* cited by examiner

HELICAL BONE FIXATION DEVICE

This application is a U.S. national stage application of International Application No. PCT/EP2014/069448, which was filed on Sep. 11, 2014, and entitled "Helical Bone Fixation Device," and which in turn claims priority to European Patent Application Number 13183883.1, filed Sep. 11, 2013, of the same title. The entire content of the aforementioned applications are herein expressly incorporated by reference.

FIELD OF INVENTION

The present invention relates generally to the field of bone fixation. More particularly, the disclosure relates to a bone fixation device comprising at least three helical slots and being arranged to expand and to fit the shape of the internal side of a vertebral pedicle. The invention also relates to a bone fixation device including bone-fixation screw, such as pedicle screw, for any application, including for example, osteosynthesis.

BACKGROUND OF INVENTION

Skeletal structures are formed of bones and adjoining structures. These skeletal structures may require artificial support or stabilization. For instance, the human spine is composed of a column of thirty-three vertebrae and their adjoining structures. Most of the vertebrae are capable of individual movement and ensure the general movement of the spine: flexion, extension, axial rotation and lateral flexion. An intervertebral disc is positioned between opposing faces of adjacent vertebrae. Each of these vertebrae includes a vertebral body, and a vertebral arch that encompass an opening, called the vertebral foramen, through which the spinal cord and spinal nerves pass. The body of the spinal vertebra is connected to the arch by the pedicles—one on each side of the vertebral arch—, which form two short thick processes.

Unfortunately, there are numerous diseases that deteriorate one or more portion of the vertebra. For example, osteoporosis, scoliosis, kyphosis, spondylolisthesis, tumors, as well as fractures or extreme shocks may leads to the deterioration of vertebrae. As a result vertebrae may collapse, nerves may be pinched causing enormous pain, or regular movement of the column may be limited. In these and other situations, surgical installation of various devices is designed to allow the person to resume a normal life.

One well-known device for spine stabilization procedures is the pedicle screw, which is threaded for engagement with bone. A pedicle screw is surgically installed posteriorly into and through a pedicle. Bone screws, like pedicle screws, are commonly used to fix adjacent bones or bone fragments with respect to each other. For example, bone screws are commonly used to help repair fractures in bone, to attach bone plates to bone, to fix adjacent vertebral bodies, or for stabilizing the spine. When the bone is diseased, for example due to osteoporosis, deteriorated, for example due to prior surgical procedure, or degenerated, securing the bone screw may be problematic. For instance, when a pedicle screw is used on osteoporotic patients, the lack of bone density makes it difficult to properly engage the bone screw threads resulting in a fragile connection between the pedicle screw and bone.

If the threaded portion of the screws does not properly secure to the bone, the bone screw will loosen and pull out or break. This loosening can occur over time. Therefore the use of bone fixation device improving the fixation between the bone and the bone screw, preferably between the vertebra and the pedicle screw, may be needed during surgical procedure.

Operation of an expandable fixation device is often carried in two steps: firstly a bone fixation device is inserted into a hole pre-drilled in the bone and secondly a bone screw, such as a pedicle screw, is inserted into the bone fixation device and ensures expansion of the bone fixation device. With this kind of devices, the bone screw is better secured by insertion into the bone fixation device, and the bone fixation device ensures fixation between the bone and the bone screw.

The bone-fixation devices of the prior art, such as for example the anchor sleeve disclosed in U.S. Pat. No. 4,711,232, are intended to expand radially their distal part upon insertion of a screw. Indeed most of the orthopedic device manufacturers are selling bone-fixation device comprising two slots defining two distal parts which spread apart from each other upon insertion of a screw; the distal parts are anchored in the cancellous vertebral body.

Each vertebra comprises a vertebral body and a vertebral arch. The vertebral body consists of cancellous bone, also named trabecular bone, having high porosity from 30 to 90%. The vertebral arch comprises two hard pedicles consisting mainly of cortical bone, also named compact bone, having low porosity from 5 to 30%.

One of the objects of the invention is therefore to enhance the fixation between the bone fixation device and the vertebra by combining an anchorage inside the soft vertebral body with an anchorage around the hard vertebral pedicle, and optionally an anchorage inside the hard vertebral pedicle. The present invention combines the expansion inside the vertebral body with an anchorage around a pedicle by squeezing the pedicle between a flange and the expanded part of the bone fixation device.

Furthermore, as disclosed herebefore, bone-fixation devices of the prior art, and especially expandable bone-fixation devices, expand radially, especially at their distal end, and thus present wide openings, hollows and asperities, into which bone may grow, preventing the ability to remove the bone-fixation devices.

As bone screws present a thread, they can be removed by unscrewing once the bone has been stabilized. The removal of the bone screw is necessary to avoid leaving unnecessarily foreign body inside the human body. The removal of the bone fixation device securing the bone screw is equally required. However the devices of the prior art with wide openings prevent or severely limit the ability to be removed after insertion.

Another object of the invention is therefore to enhance and facilitate the removal of bone-fixation devices by minimizing the openings and asperities into which bone may grow.

According to the Applicant, the present invention avoids the disadvantages of the prior art by:
  combining an anchorage inside the vertebral body with an anchorage around the pedicle and optionally an anchorage inside the pedicle; and
  minimizing the openings and asperities and allowing easy removal of the bone fixation device.

SUMMARY

The present invention relates to a bone fixation device for securing attachment between a screw and a vertebra comprising two pedicles, comprising a hollow cavity having a longitudinal axis, a distal part having itself a distal end and a proximal end, a proximal part having itself a distal end and a proximal end, and a flange at the proximal end, characterized in that:

the distal part comprises a deformable area comprising at least three helical slots; and the distal part comprises a full portion located distally after said at least three helical slots;

further characterized in that said full portion (5) cooperates with the screw such that once the screw abuts against the flange (4) of the bone fixation device (1), further screwing causes the deformation of the deformable area (2D) of the distal part (2) and the retraction of the distal end of the distal part (7) towards the proximal end of the distal part (8); and in that after screwing, the borders of each at least three helical slots (6) abuts against each other.

According to one embodiment, said bone fixation device comprises an inner threaded full portion.

According to an embodiment, said deformation of the distal part is designed to allow the deformable area of the bone fixation device to expand in the vertebral body and to press on the internal side of the vertebral pedicle, while the flange presses on the external side of the vertebral pedicle.

According to an embodiment, said proximal part further comprises at least one pedicular wing.

According to an embodiment, a wedge tapered towards the proximal end of the proximal part is located under each of said at least one pedicular wing.

According to an embodiment, said at least one wing is arranged to expand upon insertion of a mounting tool or a screw.

According to an embodiment, said proximal part is made of a biocompatible metal, alloy or polymer and the distal part is made of a biocompatible polymer.

According to an embodiment, said proximal part further comprises at least one slot for receiving an inner proximal part, made of a soft material, adapted to cover the inner surface of the proximal part, preferably the inner proximal part is made of a biocompatible polymer.

According to an embodiment, said at least three helical slots are wrapped around the distal part in the direction of the longitudinal axis.

According to one embodiment, said at least three helical slots 6 comprise a lead from 0.05 millimeter to 100 millimeters, preferably from 0.1 millimeter to 50 millimeters centimeters, preferably from 0.1 millimeter to 25 millimeters.

According to one embodiment, said at least three helical slots 6 have a width from 0 to 1 centimeter, from 0.01 to 5 millimeters or from 0.02 to 1 millimeter.

According to an embodiment, said distal part comprises 3, 4, 5, 6, 7, 8, 9 or 10 helical slots wrapped around the distal part.

According to an embodiment, said at least three helical slots are arranged so that upon deformation, the lateral sides of each of said at least three slots abut. In other words, the borders of each at least three helical slots (6) abuts against each other.

According to an embodiment, the thickness of the full portion is larger than the thickness of the rest of the distal part 2 such that the screw intended to be inserted inside the bone fixation device does not interact with the distal part except in the full portion.

The present invention also relates to a kit of parts for improving the holding strength and purchase of a screw used for the treatment of spinal disorders comprising:

at least one bone fixation device according to the present invention; and at least one bone screw designed to be used with said at least one bone fixation device of the present invention.

According to an embodiment, said kit of parts further comprises:

a tool for mounting and/or removing the bone fixation device of the present invention, wherein the tool is adapted to the shape of the flange; and a guiding pin adapted to pass through the hollow cavity of the bone fixation device and optionally to expand the at least one pedicular wing upon insertion.

DEFINITIONS

In the present invention, the following terms have the following meanings:

"Central expansion" or "helical deformation" refers to the fact that, unlike the bone fixation devices of the prior art which expand distally, the expansion occur with respect to the middle of the bone fixation device of the invention. In the present invention, central expansion refers to the deformation/expansion of the deformable area comprising helical slots. Said central expansion enables the deformed part of the deformable area to match or fit the shape of the side of the vertebral pedicle which is close to the vertebral body.

"Cooperate with or bite inside" refers to the cooperation between a screw and the inner surface of a hollow cavity (such as for example the hollow cavity of a bone fixation device). The screw may cooperate by self-tapping a thread into a smooth and untextured inner surface of the hollow cavity or the screw may cooperate with a threaded inner surface of the hollow cavity by screwing the external thread of the screw through the thread of the inner surface.

"Deformation" refers, if nothing else is specified, to the central expansion of the deformable area as defined hereabove.

"Distal" means that which is to be positioned towards the inside of the vertebra or towards the inside of the human body.

"Distal part" refers to the part of the bone fixation device which is distal. More particularly, "distal part" refers, in use, to the part situated near to the center of the vertebral body. Said distal part is inserted first into the patient vertebra.

"Expanded state" or "final anchoring position" refers to the state, position or shape of the bone fixation device after central expansion and optionally after expansion of the pedicular wings.

"Helical slot(s)" refers to the slot(s) or opening(s), passing through the matter, in the form of helix prior deformation of the device i.e. straight line(s) formed by a slit(s) or a cut(s) wrapped around and through the surface of the distal part, said straight line(s) being not parallel with the longitudinal axis of a hollow cavity.

"Internal volume" refers to the inner volume of the bone fixation device (with or without the screw inserted inside the bone fixation device).

"Lead" refers to the distance, along the longitudinal axis, which is covered by one complete rotation of one helical slot of the present invention (360°).

"Linear or longitudinal movement" refers to the screw displacement inside bone fixation device along the longitudinal axis the hollow cavity. Except otherwise specified, linear movement of the screw refers to linear movement with respect to the bone or the proximal part of the device.

"Pitch" refers, for conventional screw, to the distance from the crest of one thread to the next. In the present invention, one skilled in the art could easily understand said notion with respect to our helical slots. For single-start pitch and lead are the same. For S-start, the lead is equal to S times pitch.

"Proximal" means that which is to be positioned towards the outside of the vertebra or towards the outside of the human body.

"Proximal part" refers to the part of the bone fixation device which is proximal. More particularly, "proximal part" refers, in use, to the part situated away from the center of the vertebral body. The proximal part is inserted last into the patient vertebra and portion of the proximal part may stay outside of the vertebra after insertion. According to the present invention, proximal part refers either to the proximal part alone or to the proximal part comprising the inner proximal part.

"S-Starts" single-start means that there is only one "slot" wrapped around the hollow shaft of the bone fixation device. Double-start means that there are two "slots" wrapped around the shaft of the bone fixation device. S-start means that there are S "slots" wrapped around the shaft of the bone fixation device.

"Smaller, larger, less than or more than" refers, if nothing else is specified, to a variation of 10%, preferably 5% with respect to the initial value.

"Screw" refers to a cylinder with a helical ridge or thread running round the outside on which a rotational movement is applied allowing the thread or helical ridge to bite inside the thickness of a flexible part or to cooperate with a corresponding internal groove or thread.

BRIEF DESCRIPTION OF THE DRAWINGS

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted.

REFERENCES

Figure 1:
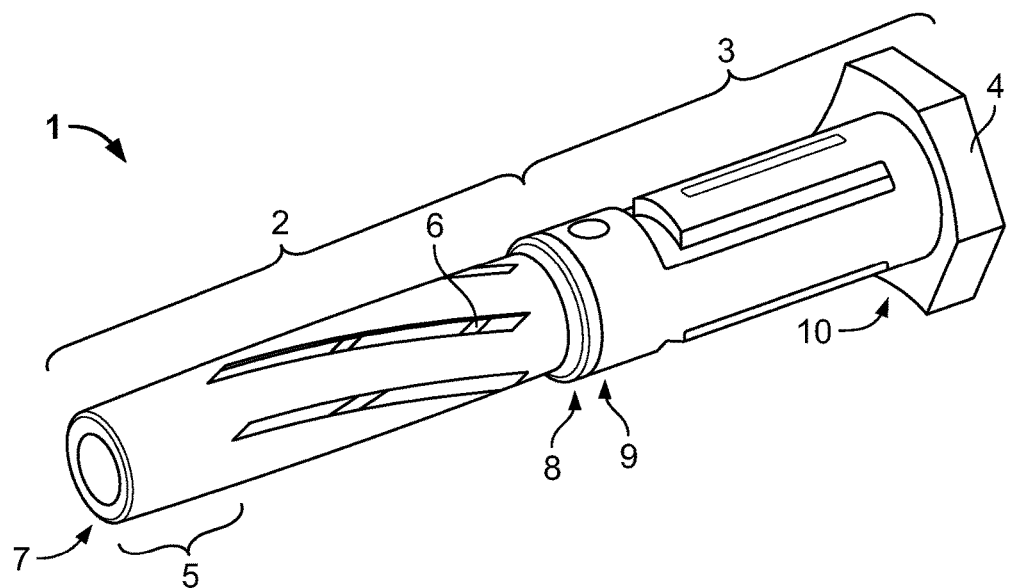
FIG. 1 represents a perspective view of the bone fixation device 1 before use, according to an embodiment of the invention.

1—Bone Fixation device
2—Distal part
2D—Deformable area
3—Proximal part
4—Flange or collar
5—Full portion of the distal part
6—Helical slots or openings
7—Distal end of the distal part
8—Proximal end of the distal part
9—Distal end of the proximal part
10—Proximal end of the proximal part
11—Pedicular wing
12—Wedge
13—Inner proximal part
14—Recess
15—Slot separating the proximal part from the pedicular wing
16—Slot or recess for connecting the inner proximal part to the proximal part
100—Screw
200—Vertebra
201—Vertebral pedicle

DETAILED DESCRIPTION

This invention generally relates to a bone fixation device comprising a hollow cavity having a longitudinal axis, a distal part and a proximal part; said distal part comprising at least three helical slots.

According to one embodiment, the bone fixation device comprises a hollow cavity, said cavity may have any shape that a person skilled in the art would find suitable; preferably said cavity is a tubular cavity or a hollow shaft.

The bone fixation device of the invention is designed to be positioned between the shaft of a screw and surrounding bone tissue to increase the holding strength of a screw. Presence of the screw inside the bone fixation device also enhances mechanical properties of the assembly (i.e. screw and bone fixation device), particularly pull-out strength.

The bone fixation device is designed to receive a screw, preferably a bone screw, more preferably a pedicle screw. When a screw is inserted into the bone fixation device, at least a portion of the bone fixation device expands. Said expansion—referred to as central expansion—being arranged so that the expanded or deformed part fit the shape of the side of a vertebral pedicle which is close to the vertebral body.

The bone fixation device comprises a flange on the proximal part. Upon insertion of a bone screw central expansion occurs, squeezing hardly the pedicle between the flange on the proximal side of the vertebra and the expanded part on the distal side of the pedicle; therefore securing the bone fixation device with respect to the vertebra thanks to the hard vertebral pedicle.

Moreover, the bone fixation device of the present invention may comprise at least one pedicular wing on the proximal part; upon insertion of the bone screw, said at least one pedicular wing expands and bites in the inner surface of the pedicle, therefore securing even more the bone fixation device with respect to the vertebra.

The bone fixation device of the present invention allows securing the bone screw with respect to the bone thanks to:
  optionally at least one pedicular wing located on the proximal part and which expands and bites the inner surface of the pedicle; and/or
  central expansion of the bone fixation device which allows:
    to expand the bone fixation device in the vertebral body and to anchor it with respect to the vertebral body;
    to squeeze the pedicle between on one side the flange and on the other side the expanded or deformed part.

Furthermore, the bone fixation device may be removed easily if needed due to the at least three helical slots abutting against each other during use and the at least one pedicular wing expanded towards the distal part, thereby facilitating the removal.

The bone fixation device is more particularly designed for use with bone-fixation screws, such as pedicle screws of any model, for any application, including for example, osteosynthesis.

The bone fixation device is more particularly designed for insertion into and through a vertebral pedicle.

FIG. 1 discloses the overall structure of the invention. The bone fixation device 1 of the present invention comprises a hollow cavity having a longitudinal axis, a distal part 2 and a proximal part 3. Said proximal part 3 comprises at its proximal end 10 a flange 4. Said distal part 2 comprises at its distal end 7 a full portion 5 and, along the distal part and in the direction of the longitudinal axis at least three helical slots 6. The proximal end of the distal part 8 and the distal end of the proximal part 9 are connected in order to form an integral part: the bone fixation device 1 of the invention.

The different parts of the present invention will now be fully described.

Distal Part

According to one embodiment, the distal part 2 is arranged so that to be, in use, mainly or predominantly intra-somatic. According to one embodiment, the distal part 2 comprises distally a full portion 5 (i.e. a portion without slots) and proximally a deformable area 2D comprising at least three helical slots 6.

According to one embodiment, as seen in FIG. 1, the distal part 2 comprises helical slot(s), preferably at least three openings or slots 6 in the shape of a helix in the non-expanded state (i.e. before use). According to one embodiment, the bone fixation device 1 also comprises helical slot(s) 6 in use (i.e. in the expanded state). Preferably the distal part 2 comprises at least three slots 6 in the shape of a helix in the direction of the longitudinal axis of said hollow cavity. According to one embodiment, said at least three helical slots 6 defined a deformable area 2D in the distal part 2. According to one embodiment, said helical slots 6 are wrapped and oriented in the direction of screwing. Thus the at least three helical slots 6 twist in two possible directions (right-handed or left-handed slots), depending of the helix of the thread of the screw to be secured within the bone fixation device 1. If the screw has a right-handed thread, the bone fixation device 1 comprises right-handed slots and if the screw has a left-handed thread, the bone fixation device 1 comprises left-handed slots.

According to one embodiment, said helical slots 6 present S-starts, S being equal to 3 (3 helical slots), 4 (4 helical slots), 5 (5 helical slots), 6 (6 helical slots), 7 (7 helical slots), 8 (8 helical slots), 9 (9 helical slots) or 10 (10 helical slots). According to one embodiment, the distal part 2 comprises 3, 4, 5, 6, 7, 8, 9 or 10 helical slots (6) wrapped around the distal part along the longitudinal axis of the hollow cavity. According to one embodiment, said at least three helical slots 6 start close to the proximal end of the distal part 8. According to one embodiment, said at least three helical slots 6 start at the proximal end of the distal part 8. According to one embodiment, the at least three helical slots 6 start at the same level along the longitudinal axis. According to one embodiment, the at least three helical slots 6 start at different levels along the longitudinal axis. According to an embodiment, the distal part 2 comprises 1 or 2 helical slot(s). According to an embodiment, the distal part 2 does not comprise 1 or 2 helical slot(s).

According to one embodiment, said at least three helical slots 6 comprise a lead from 0.05 millimeter to 100 millimeters, preferably from 0.1 millimeter to 50 millimeters centimeters, preferably from 0.1 millimeter to 25 millimeters. According to one embodiment, said at least three helical slots 6 have a pitch from 2 millimeters to 100 centimeters, preferably from 3 millimeters to 10 centimeters.

According to one embodiment, said at least three helical slots 6 have a width from 0 to 1 centimeter, from 0.01 to 5 millimeters or from 0.02 to 1 millimeter. According to the embodiment wherein the width of the at least three helical slots is 0 means that a mere cut through the distal part 2 is performed.

According to one embodiment, the at least three helical slots 6 end before one full lead. According to one embodiment, the at least three helical slot 6 ends before one full pitch.

According to one embodiment, the at least three helical slots 6 end from 0.1 millimeter to 5 centimeters, from 0.5 millimeter to 2 centimeters or from 1 millimeter to 1 centimeter or from 1 millimeter to 5 millimeters before the distal end of the distal part 7 in order to strengthen said distal portion and to define a so-called full portion 5.

According to one embodiment, the full portion 5 is located distally after the at least three helical slots 6.

According to one preferred embodiment, helical slots 6 are contiguous in use i.e. in the final anchoring position, thus preventing bone growth inside the distal part 2.

According to one preferred embodiment, helical slots 6 are closed against each other in use i.e. in the final anchoring position, thus preventing bone growth inside the distal part 2.

Figure 6:
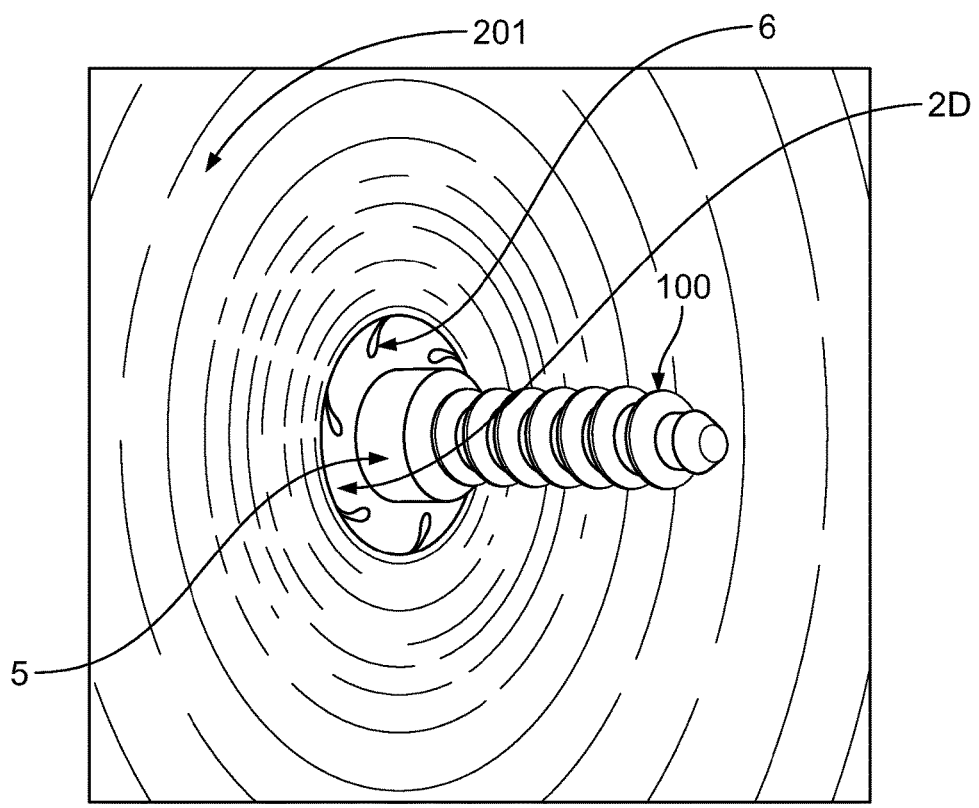
FIG. 6 represents a photography from the inside of a vertebra of the bone fixation device 1 in use with a bone screw in the final anchoring position, wherein the helical slots abut against each other.
Figure 7:
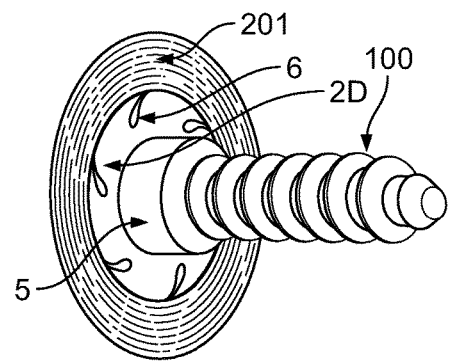
FIG. 7 represents a perspective view from the inside of a vertebra of the bone fixation device 1 in use with a bone screw in the final anchoring position, wherein the helical slots abut against each other.

According to one embodiment—as seen in FIGS. 6 and 7, the lateral sides of the at least three helical slots 6 come closer during deformation of the deformable area 2D and are contiguous in the final anchoring position of the bone fixation device 1.

According to one preferred embodiment, the expanded state of the bone fixation device 1 is designed for preventing bone growth inside the bone fixation device 1, more particularly inside the deformable area 2D.

According to one preferred embodiment, helical slots 6 are designed and adapted to leave less space possible for bone growth, more preferably the expanded state of the deformable area 2D prevents gap regions.

According to one embodiment, the internal volume of the bone fixation device 1 is isolated from the surrounding bone tissue when the screw is inserted allowing central expansion. Bone tissue cannot penetrate the internal volume of the bone fixation device 1 in its expanded state. Indeed, the screw is inserted, reaches and bites/cooperates with the inner surface of the full portion 5 in such a way that the connection between the screw and the full portion 5 isolates the internal volume from the surrounding bone tissue. Moreover, in the expanded state, helical slots 6 are contiguous thereby isolating the internal volume of deformable area 2D.

Figure 3:
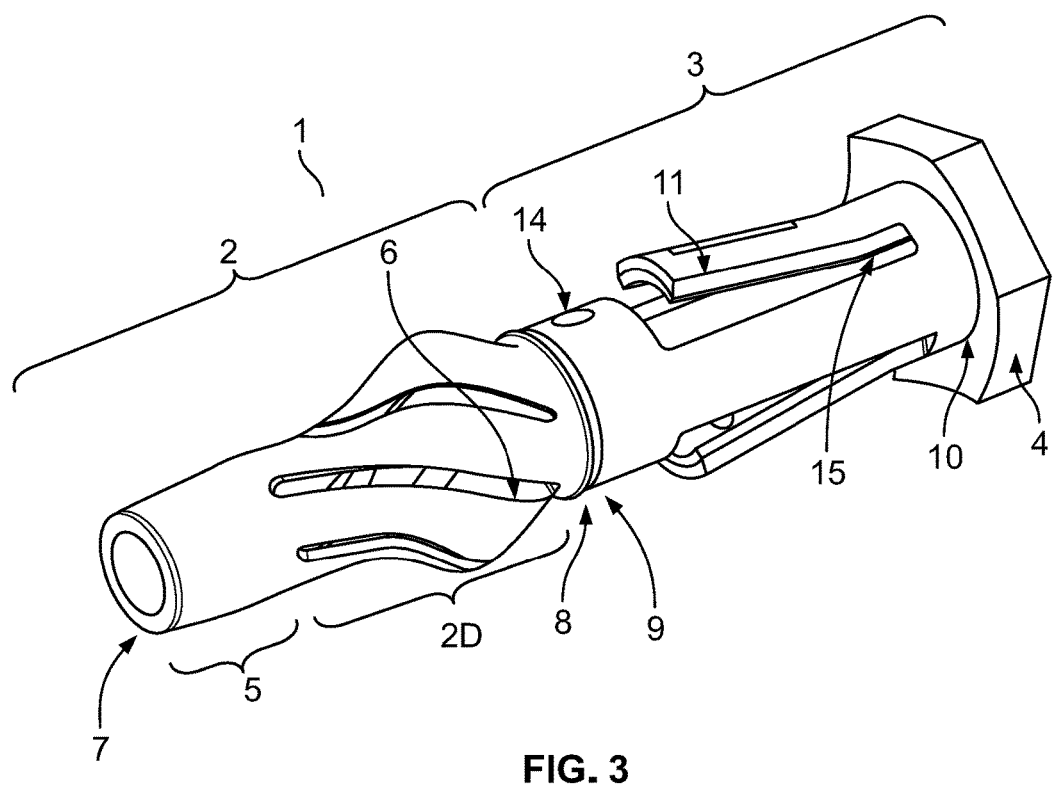
FIG. 3 represents a perspective view of the bone fixation device 1 in use, according to an embodiment of the invention (the bone screw is not shown).
Figure 4:
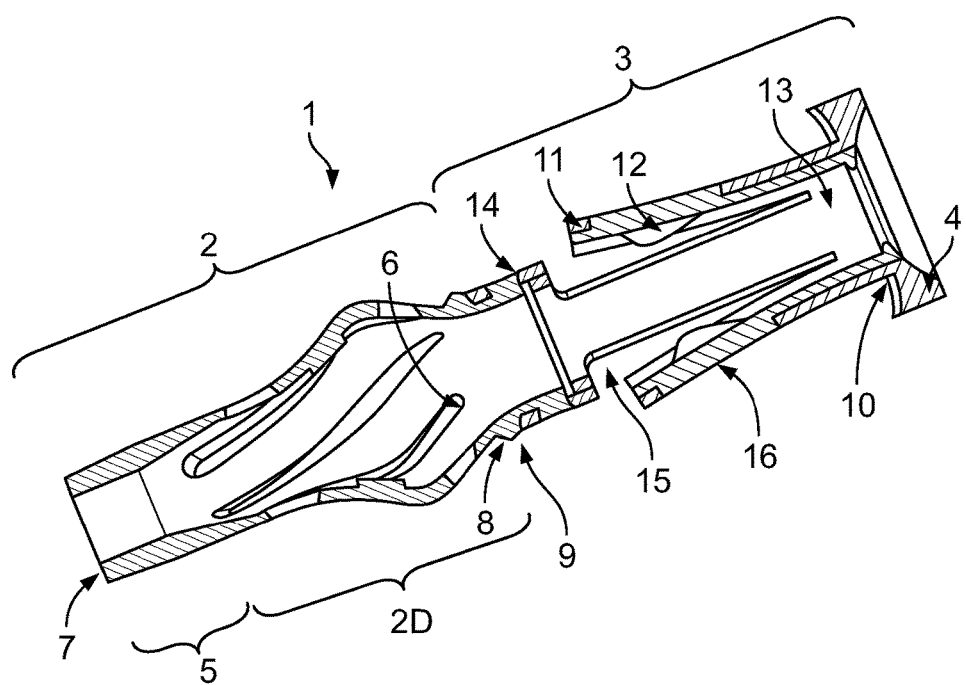
FIG. 4 represents a sectional perspective view of the bone fixation device 1 in use, according to an embodiment of the invention (the bone screw is not shown).
Figure 5:
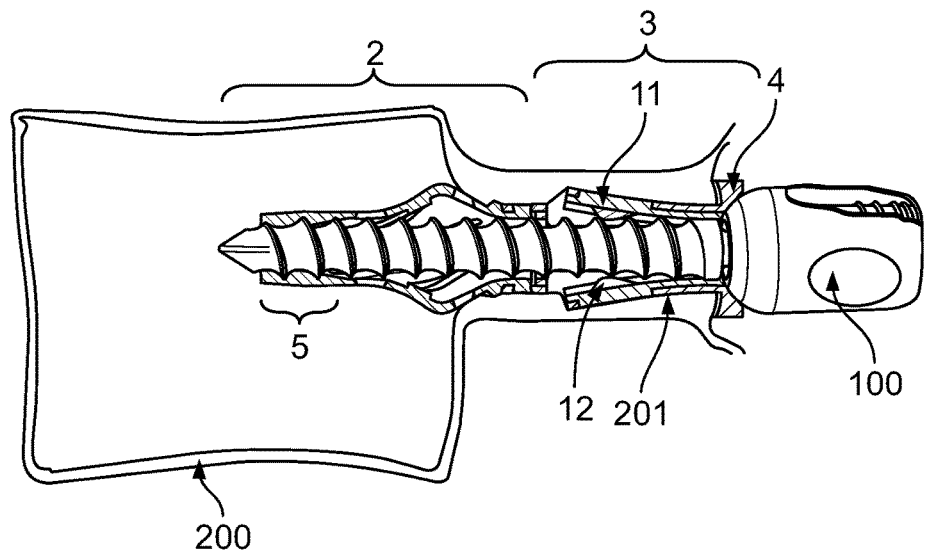
FIG. 5 represents a sectional perspective view of the bone fixation device 1 in use with a bone screw, according to an embodiment of the invention.

The specific helical slots 6 design ensures that anchoring of the bone fixation device 1 (as seen in FIGS. 3, 4 and 5) is due to central expansion of the deformable area 2D. The removal of the bone fixation device 1 is efficiently facilitated due to the specific helical slots 6 design preventing gap regions, openings, hollows and asperities into which bone may grow.

According to one embodiment, as seen in FIG. 1, the distal part 2 comprises a full portion 5 located distally after the helical slots 6.

According to one embodiment, the full portion 5 does not comprise helical slots 6.

According to one embodiment, the full portion 5 is a hollow cavity i.e. with at least one opening located at the distal end of the full portion 5, more particularly in the distal end of the distal part 7. According to another embodiment, the full portion 5 is not a blind cavity i.e. without opening located at the distal end of the full portion. In a preferred embodiment, the full portion 5 is designed for allowing a screw to bite/cooperate along the entire length of the full portion 5.

According to one embodiment, the inner surface of the full portion 5 is adapted for cooperating with a screw. In a preferred embodiment, inner surface of the full portion 5 is threated. According to another embodiment, inner surface of the full portion 5 is smooth, unruffled or not textured.

According to an embodiment, the inner surface of the full portion 5 is threaded in such a way that the inner surface of the full portion 5 and the screw are threadably connected. "Threadably connected" means that pitch and dimensions of the screw are compatible with pitch and dimensions of the threaded inner surface of the full portion 5 and thus allows a screwing movement of the screw inside the full portion 5. According to one embodiment, the full portion 5 comprises an inner thread.

According to an embodiment, the inner surface of the full portion 5 is smooth, unruffled or not textured in such a way that insertion of a screw inside the full portion 5 cuts the inner surface of the full portion 5 and then taps a thread in the distal full portion 5. Thus, the inner surface of the full portion 5 and the screw are threadably connected.

According to a preferred embodiment, the full portion 5 is compatible with bone screws available on the market, particularly pedicular screws.

According to one embodiment, the full portion 5 of the distal part 2 does not comprise a thread or a nut.

Figure 2:
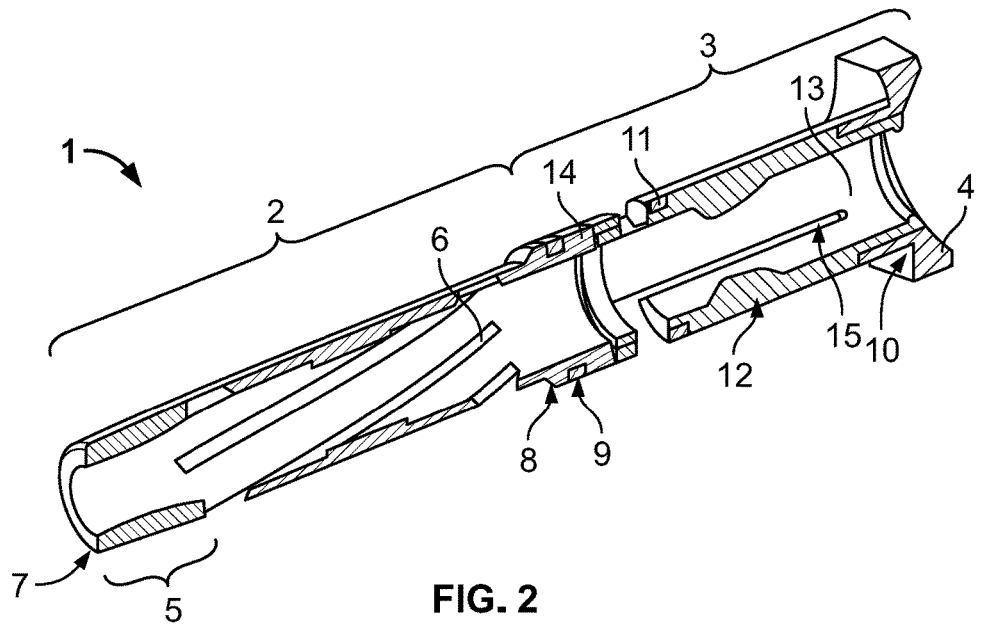
FIG. 2 represents a sectional perspective view of the bone fixation device 1 before use, according to an embodiment of the invention.

As disclosed in FIG. 2, the distal part 2 comprises, before use, a constant external diameter. According to one embodiment, the distal part 2 comprises, before use, a substantially uniform outer diameter.

According to one embodiment, the distal part 2 of the bone fixation device 1 comprises, before use, an internal diameter (measured outside of the full portion 5) being substantially equal to the external diameter of the bone screw (thread diameter or crest diameter, i.e. the height of the thread being included) intended to be inserted in said bone-fixation device 1. According to one embodiment, the distal part 2, except for the full portion 5 comprises, before use, a constant inner diameter. According to one embodiment, the distal part 2, except for the full portion 5, comprises, before use, a substantially uniform inner diameter.

According to a preferred embodiment, the distal part 2 of the bone fixation device 1 comprises, before use, an internal diameter (measured outside of the full portion 5) being larger than the external diameter of the bone screw (thread diameter or crest diameter, i.e. the height of the thread being included) intended to be inserted in said bone-fixation device 1.

According to one embodiment, the distal part 2 of the bone fixation device 1 comprises, before use, an internal diameter (measured outside of the full portion 5) being substantially equal to the diameter of the shaft of the bone screw (i.e. the root diameter of a bone screw) intended to be inserted in said bone-fixation device 1.

According to one embodiment, the distal part 2 of the bone fixation device 1 comprises, before use, an internal diameter (measured outside of the full portion 5) being larger than the diameter of the shaft of the bone screw (i.e. the root diameter of a bone screw) intended to be inserted in said bone-fixation device 1.

As seen in FIG. 2, the thickness of the full portion 5 is larger than the thickness of the rest of the distal part 2. In a preferred embodiment, the full portion 5 of the distal part 2 comprises a smaller internal diameter than the internal diameter of the rest of the distal part 2, defining an extra-thickness. Said extra-thickness is designed in such a manner that the thread of a bone screw could, in use, interact with (i.e. bites inside/cooperates with) and be anchored in the extra-thickness of said full portion 5 The extra-thickness is designed for being either threaded (and then compatible with the screw pitch) or smooth, unruffled (and then designed for allowing the screw to cut the extra-thickness and to tap a thread). In said embodiment, the internal diameter of said full portion 5 is substantially equal or less than the external diameter of the bone screw (thread diameter or crest diameter, i.e. the height of the thread being included) intended to be inserted in the bone fixation device 1 of the present invention. According to one embodiment, the internal diameter of said full portion 5 is substantially equal or less than the diameter of the shaft of the bone screw (root diameter, i.e. the height of the thread being excluded) intended to be inserted in the bone fixation device 1 of the present invention. According to one embodiment, the screw may interact with (i.e. bites inside or cooperates with) the full portion 5 but does not interact with the deformable area 2D.

According to one embodiment, the inside of the distal part 2 is not tapered. According to one embodiment, the inside of the distal part 2 is not tapered along the whole distal part. According to one embodiment, the inside of the distal part 2 is proximally tapered through the whole distal part. As disclosed in FIG. 2, the inside of the distal part 2 is tapered between the previously disclosed full portion 5 and the inner diameter of the rest of the distal part 2 along less than one centimeter, preferably along 5 millimeters, more preferably along 2 millimeters.

According to one embodiment, said full portion 5 covers from 0.1 millimeter to 10 centimeters, from 0.1 millimeter to 3 centimeters, from 1 millimeter to 2 centimeters or from 2 millimeters to 1 centimeter from the distal end of the distal part 7.

According to one embodiment, the distal part 2 has a thickness (measured outside of the full portion 5) from 0.1 millimeter to 10 millimeters, from 0.5 millimeters to 5 millimeters, or from 1 millimeter to 3 millimeters. According to one embodiment, the full portion 5 has a thickness from 0.1 millimeter to 15 millimeters, from 1 millimeter to 6 millimeters, or from 2 millimeters to 4 millimeters.

The bone fixation device 1 of the present invention may be made from various biocompatible materials and combinations of biocompatible materials. According to one embodiment, the distal part 2 and the proximal part 3 of the bone fixation device 1 are made from the same material or from different materials. According to one embodiment, the distal part 2 of the bone fixation device 1 is made from a single or from various materials. According to one embodiment, the materials of the deformable area 2D and of the full portion 5 are the same or are different. Suitable material includes tissue friendly metals, alloys, composite, polymers or reinforced polymers which are commonly used in surgical implants and that one skilled in the art would be known to have sufficient strength to meet the objectives of the invention.

Numerous high strength polymers are employed to make implants such as polyetheretherketone (PEEK), epoxys, polyurethanes, polyesters, polyethylenes (PE), vinyl chlorides, polysulfones, polytetrafluoro-ethylene (PTFE), polycarbonates, carbon fiber polyester, polyaryetherketone (PAEK), polyoxymethylene, nylon, polyetherketoneetherketoneketone (PEKEKK), silicones and the like. According to one embodiment, the distal part 2 of the bone fixation device 1 is made from one of the previously disclosed polymers or from a material that one skilled in the art would find suitable, preferably from PEEK.

According to one embodiment, the distal part 2 is designed to be more deformable than the proximal part 3. Said embodiment is performed due to the design of the distal and proximal part (2, 3) (e.g. due to the helical slots) and/or the materials of the distal and proximal part (2, 3).

According to one embodiment, the distal part 2 is designed to be at least partially less rigid than the proximal part 3. Said embodiment enables the screw to self-tap a thread inside the distal part 2, preferably in the full portion 5, more preferably in the extra-thickness of the full portion 5. Said embodiment is also performed due to the ability of the deformable area 2D to be deformed.

FIGS. 3, 4 and 5 show the bone fixation device 1 of the invention, in use, and highlight the function of the device.

According to one embodiment, upon insertion of a screw 100 into the core of the hollow cavity of the bone fixation device 1, the screw 100 (i) reaches the full portion 5 of the distal part 2 of the bone fixation device 1, (ii) bites in/cooperates with the extra-thickness of the full portion 5 and then (iii) by further screwing the distal end of the distal part 7 moves backwards towards the proximal part 3, thereby deforming the deformable area 2D of the bone fixation device 1 and ensuring secure fixation with the surrounding tissue. After a certain amount of retraction, the bone fixation device 1 locks up into its folded position when the expanded or deformed deformable area 2D squeezes against one side (the internal side or distal side or side close to the vertebral body) of the vertebral pedicle 201.

According to one embodiment, once the head of the screw 100 abuts against the flange 4 of the proximal part 3, further screwing does not cause distal (i.e. linear) displacement of the screw with respect to the proximal part 3. Further screwing causes the full portion 5 of the distal part 7 to move backwards to the proximal part 3 due to screwing without longitudinal displacement of the screw 100 with respect to the proximal part 3.

According to one embodiment, the screw 100 is first inserted into the opening located at the proximal end of the proximal part 10 and is screwed leading to a distal (i.e. linear) movement of the distal end of the screw 100 relative to the proximal part 3. The screw may optionally abut against at least one wedge 12 thus expanding the pedicular wings 11. The screw 100 then penetrates into the distal part 2 until the full portion 5 and bites inside/cooperates with the full portion still leading to a distal (i.e. linear) movement of the distal end of the screw 100 relative to the proximal part 3. When the head of the screw 100 abuts against the flange 4 of the present invention, said flange 4 immobilizes the screw with respect to the bone and prevents the distal linear movement of the screw relative to proximal part 3. According to the principle of the worm drive, further turning/screwing the screw 100 leads the distal end of the screw 100 to cooperate with the thickness of the full portion 5 without displacement of the screw with respect to the proximal part 3, more particularly with respect to the flange 4. This cooperation with the full portion 5 without linear movement of the screw 100 relative to the proximal part 3 causes the deformation of the deformable area 2D of the distal part 2, wherein the distal end of the distal part 7 retracts towards the proximal end of the distal part 8.

According to a preferred embodiment, the screw 100 bits inside/cooperates with the thickness of the full portion 5 and no central expansion occurs during this step until the head of the screw 100 is blocked in translation against the flange 4. Thus the expansion step begins wherein turning the head of the screw 100 without linear movement of the screw relative to the proximal part 3 simultaneously leads to central expansion.

According to one embodiment, the screw 100 is pushed up by twisting which causes a linear distal movement of the screw relative to the proximal part 3 inside the full portion 5 and then central expansion of the distal part 2 occurs by further push up the screw 100 by twisting without distal (i.e. linear) movement relative to the proximal part 3.

According to one embodiment, said screw (especially the head of the screw) lies against the inner surface of the flange 4 thereby preventing longitudinal movement of the screw 100 relative to the proximal part 3.

According to an embodiment; a linear movement of the screw 100 freely mobile (i.e. without connection with the full portion 5) into the hollow cavity of the present invention does not allow central expansion.

According to one embodiment, pulling the screw 100 through bone fixation device 1 does not allow central expansion.

According to one embodiment, pushing the screw 100 through bone fixation device 1 does not allow central un-expansion.

According to one embodiment, the screw 100 inserted into the present invention allows deformation of the deformable area 2D is not an actuator, for example a partially threaded rod, a control wire or a pin.

According to one embodiment, said screw 100 is not an actuator which is only moving linearly, i.e. along the longitudinal axis without rotational movement more particularly without being screwed.

According to one other embodiment, the bone fixation device 1 is compatible with a screw 100 which is uniformly threaded throughout.

According to one other embodiment, the present invention is compatible with a screw 100 having a uniform pitch throughout the length. According to a preferred embodiment, the screw 100 does not comprise at least 2 different pitches throughout its length.

According to one embodiment, the bone fixation device 1 does not comprise an inner thread in the proximal part 3. According to one embodiment, the bone fixation device 1 does not comprise inner thread. According to one embodiment, the bone fixation device 1 comprises a single inner thread inside the full portion 5.

According to one embodiment, the full portion 5 does not expand radially.

According to one embodiment, the full portion 5 is not designed for being only a locking means for locking the bone fixation device 1 into an expanded state.

According to one embodiment, the central expansion does not occur by means of a difference between pitches throughout the length of the screw.

The at least three helical slots 6 present many advantages:
- the deformable area 2D of the distal part 2 may be deformed helically,
- the deformable area 2D of the bone fixation device 1 may expand,
- the distal part 2, preferably the deformed or expanded deformable area 2D, may easily fit the profile against which it is based (i.e. the profile of the vertebral pedicle, preferably the profile of the side of the vertebral pedicle close to the vertebral body),
- the lateral sides of the at least three helical slots 6 can, during deformation, come closer and become contiguous, thus avoiding non-desired growth of bone inside the bone fixation device 1.

In one embodiment, the outer walls of the distal part 2 of the bone fixation device 1 can be ribbed, threaded, fretted or otherwise textured to enhance the fixation to the bone. In another preferred embodiment, the outer walls of the distal part 2 is smooth, unruffled or not textured; minimizing the damages to bone tissue and facilitating the removal of the bone fixation device 1 after use.

According to one embodiment, the distal part 2 does not comprise hinges but at least three helical slots. In the case of hinges, the distal part moves backwards towards the proximal part 3 as in the present invention, but also retracts laterally offering wide openings for bone growth inside the distal part. In the present invention, the distal part 2 retracts helically and does not offer wide openings for bone growth inside the distal part 2.

In the present invention the at least 3 helical slots 6 will (i) limit the radial expansion as the distal part 2 will be deformed helically, (ii) facilitate the shaping along the vertebral pedicle as the at least three helical slots 6 offers more flexibility to the distal part 2 and (iii) avoid wide openings as, during retraction of the distal part 2 towards the proximal part 3, the lateral sides of the at least three helical slots 6 will abut and become contiguous.

According to one embodiment, the distal part 2 close to the distal end of the distal part 7 (i.e. the full portion 5) is not configured to expand more than the proximal part 3. However, the distal part 2 close to the proximal end of the distal part 8 (i.e. the deformable area 2D) is configured to expand more than the proximal part 3.

According to one embodiment, the distal part 2 comprises wings or blades. According to one embodiment, the distal part 2 does not comprise wings or blades. According to one embodiment, the bone fixation device 1 is generally tapered. According to one embodiment, the bone fixation device 1 is not generally tapered. In one embodiment, the full portion 5 of the distal part 2 is not designed to break upon insertion of a screw. According to one embodiment, the bone fixation device 1 does not comprise blades which move apart laterally upon insertion of the bone screw 100. According to one embodiment, the bone fixation device 1 is not distally expandable. According to one embodiment, the bone fixation device 1 of the present invention does not intend to be only anchored with respect to the vertebral body but preferably also with respect to the hardest part of the vertebra: the pedicle.

According to one embodiment, the bone fixation device 1 of the present invention does not intend to be only anchored with respect to a bone without a screw 100. According to one embodiment, the bone fixation device 1 of the present invention is intended to be exclusively associated with a screw 100.

Proximal Part

According to one embodiment, the proximal part 3 is arranged so that to be, in use, mainly or predominantly intra-pedicular.

In one embodiment, the outer walls of the proximal part 3 of the bone fixation device 1 can be ribbed, threaded, fretted or otherwise textured to enhance the fixation to the bone. In another preferred embodiment, the outer walls of the proximal part 3 may be smooth, unruffled, or untextured; thus minimizing the damages to bone tissue and facilitating the removal of the bone fixation device 1 after use. According to one embodiment, the outer walls of the bone-fixation device 1 do not comprise true bulk thread; thus minimizing damages to the bone tissue.

According to one embodiment, the proximal part 3 comprises anti-rotation ridges located close to the proximal end of the proximal part 10.

According to a preferred embodiment, the bone fixation device 1 comprises at the proximal end of the proximal part 10 a radially projecting flange or collar 4. Said flange 4 prevents advancement of the bone fixation device 1 into the pre-drilled hole of the vertebra. The flange 4 serves to provide a stop for the bone fixation device 1 to allow it to rest on the cortical surface of the bone or to hold down a plate or other implant device. Various features can be designed into the flange 4 or on the circumference of the flange 4 for driving it into the operating area and, if needed, out of the operating area. This can include hexes, notches, slots and the like, either internal or external, sized to mate with appropriate tools for implanting the sleeve into a pre-drilled hole in the operating area. According to one embodiment, the flange 4 is adapted to the bone surface. According to one embodiment, the flange 4 may be asymmetrical in order to better support or rest on the surrounding bone.

According to one embodiment, the proximal part 3 is, in use, immobilized relative to the bone due to the flange 4 lying against the bone surface.

According to one other embodiment, the flange 4 is directly laid against the bone surface, without any locking mechanism for example a washer.

According to one embodiment, the flange 4 of the proximal part 3 blocks the head of the screw enabling deformation of the deformable area 2D of the distal part 2 by retracting distal end of the distal part 7 toward the proximal end of the distal part 8 during screwing.

According to a preferred embodiment (as seen, before use, in FIG. 2, and, in use, in FIG. 3), the bone fixation device 1 comprises on the proximal part 3 at least one pedicular wing 11, preferably two or four pedicular wings 11. According to a preferred embodiment, the pedicular wings 11 are diametrically opposed. According to one embodiment, the pedicular wings 11 are not located on the distal part 2.

According to one embodiment, only the proximal part 3 comprises a second anchoring mechanism, especially at least one pedicular wing 11. According to preferred embodiment, the second anchoring mechanism, especially the at least one pedicular wing is designed for being anchored into the hard pedicle vertebra 201.

According to one embodiment, the at least one pedicular wing 11 is designed to expand inside the vertebral pedicle.

According to one embodiment, the at least one pedicular wing 11 may have various shapes, such as a strip, preferably a rectangular strip or a helical strip. According to one embodiment, the pedicular wing 11 may be helical along the same direction as the at least three helical slots 6 of the distal part 2 thus facilitating the removal. According to one embodiment, the pedicular wing 11 may be helical and oriented as the at least three helical slots 6.

According to one embodiment, the at least one pedicular wing 11 is connected to the proximal part 3 only by one side, preferably its proximal side; the other sides being free and separated from the proximal part 3 of the bone fixation device 1 by a slot 15 (as seen in FIG. 2).

According to one embodiment a wedge 12 is located under each of said pedicular wings 11. Said wedge 12 being triangularly shaped and located such that the thicker portion is located distally. According to one embodiment, the wedge 12 is tapered towards the proximal end of the proximal part 10. According to one embodiment, the wedge 12 becomes thinner as it approaches the proximal end of the proximal part 10. According to one embodiment, the pedicular wing (11) and the wedge (12) are attached together or form an integral part.

Figure 9:
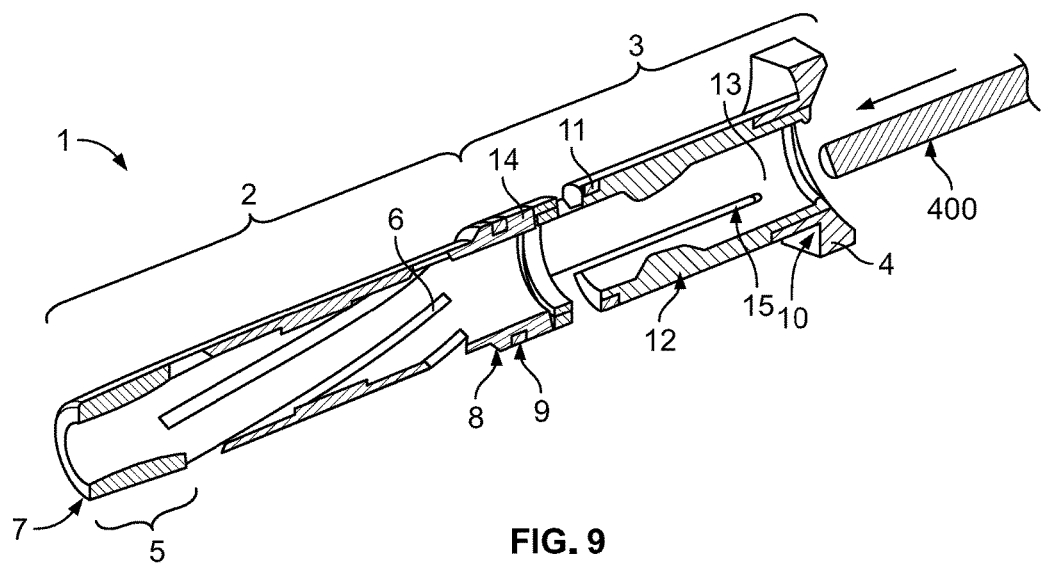
FIG. 9 represents the perspective view of FIG. 2 with a guide pin positioned relative to the bone fixation device 1.

According to one embodiment, the wedge 12 is sized such that each pedicular wing 11 may expand upon insertion of a device (a screw 100 or a mounting tool such as guide pin 400 shown in FIG. 9), and may bite the pedicles therefore securing the bone fixation device 1. According to one embodiment, the wedges 12 are not intended to be a locking means compatible with a particular screw, such as a screw with a recess designed for receiving a wedge or a tap. On the contrary, the wedges 12 are sized such that they can be used with any conventional screw.

According to one embodiment, upon insertion of a bone screw 100, the at least one pedicular wings 11 is actuated (due to the wedge 12) and expands inside the pedicle of the patient. According to another embodiment, the expansion of the at least one pedicular wing 11 is performed before screwing the bone screw 100 in order to avoid rotation of the bone fixation device 1 when screwing. The expansion of the at least one pedicular wing may be performed before insertion of the screw 100 by a mounting tool.

According to an embodiment, the bone fixation device 1 comprises two pedicular wings 11, diametrically opposed, the first pedicular wing 11 being actuated before the second because the screw 100 or the mounting tool will reach the first pedicular wing 11 before it reaches the second pedicular wing 11. This sequential actuation is particularly useful to prevent rotation of the bone fixation device 1 when a screw 100 is inserted into the cavity of the bone fixation device 1.

According to one embodiment, the outer walls of the at least one pedicular wing 11 can be ribbed, threaded, fretted or otherwise textured to enhance the fixation to the vertebral pedicle. In another preferred embodiment, the outer walls of the at least one pedicular wing 11 is smooth, unruffled or not textured.

According to one embodiment (as seen in FIG. 2), the proximal part 3 comprises close to its distal end 9 at least one recess 14. According to one embodiment, said at least one recess 14 may be in any form that one skilled in the art would find suitable such as for example a circular groove substantially perpendicular to the axis of the bone fixation device 1, a hole in the form of a disc or combination thereof.

According to one embodiment, the proximal part 3 is made from a biocompatible metal or alloy. According to one embodiment, the proximal part 3 of the bone fixation device 1 is made from a single or various materials. In a preferred embodiment, the proximal part 3 is made from titanium. According to another embodiment, the proximal part 3 is made from a titanium alloy, a cobalt alloy, a stainless steel alloys, or a combination thereof. According to one embodiment, the proximal part 3 may be plastically deformed. According to one embodiment, the proximal part 3 is not designed to be deformed, except the at least one pedicular wing 11 designed to be expanded. According to one embodiment, the proximal part 3 is made from a biocompatible polymer chosen among those used for the distal part 2. In said embodiment, the proximal part 3 may be made from PEEK or other polymers that one skilled in the art would find suitable. According to one embodiment, the proximal part 3 is made from a biocompatible metal, alloy or polymer.

According to one embodiment, some parts of the bone fixation device 1 can incorporate X-ray blocking material, thereby accurately ascertaining the presence and location of the bone fixation device 1.

According to the Applicant the combination of a rigid structure made of biocompatible metal, alloy or polymer for the proximal part 3—intended to be partly inserted inside the vertebral pedicle—, and of a deformable structure made of biocompatible polymer for the distal part 2—intended to partly expand inside the soft vertebral body—, is particularly advantageous in order to minimize the trauma to the vertebra while optimizing the anchorage and the efficiency of the bone fixation device 1. According to an embodiment, the distal part 2 and the proximal part 3 are made from different or the same polymer and does not present the same rigidity due to a rigid structure for the proximal part 3 and a deformable structure for the distal part 2.

According to one embodiment, the proximal part 3, made from a metal, an alloy or a polymer comprises an inner proximal part 13 made from a polymer, facilitating the insertion of the bone screw 100, and covering the inner surface of the proximal part 3.

According to another embodiment, the proximal part 3, made from a metal, an alloy or a polymer, comprises an outer proximal part made from a polymer and covering the outer surface of the proximal part 3.

According to one embodiment (as seen in FIG. 2), the proximal part 3 may comprise at least one slot or a recess 16 for receiving the inner proximal part and allowing the fixation of the inner proximal part 13 to the proximal part 3. Said slot or recess 16 is preferably a slot located along each pedicular wing 11.

According to one embodiment, the inner proximal part 13 is designed to be inserted inside the proximal part 3 and to be secured with respect to the proximal part 3 due to the at least one slot or recess 16.

According to one embodiment, the at least one pedicular wing 11 is located in the hard proximal part 3 while the wedge 12, located under each pedicular wing 11, is located in the soft inner proximal part 13. Alternatively, the at least one pedicular wing 11 and the wedge 12 may be located in the hard proximal part 3.

According to one embodiment, the inner proximal part 13 of the bone fixation device 1 is made from one of the previously disclosed polymers or from a material that one skilled in the art would find suitable, preferably from PE. According to one embodiment, the inner proximal part (13) is made from a material which is different or the same as the material of the proximal part (3), preferably a different material.

According to an embodiment, the inner proximal part (13) is made from a softer material than the material of the proximal part (3).

According to one embodiment, the proximal part 3 without the inner proximal part 13 has preferably a thickness from 0.1 millimeters to 5 millimeters, preferably from 0.5 millimeter to 2 millimeters.

According to one embodiment, the inner proximal part 13 has preferably a thickness from 0.1 millimeters to 5 millimeters, preferably from 0.5 millimeter to 2 millimeters.

Bone Fixation Device

FIGS. 1 and 2 show the bone fixation device 1 before use.

According to one embodiment, the distal part 2 and the proximal part 3 form an integral part. According to one embodiment, the distal part 2 and the proximal part 3 are securely fixed. According to one embodiment, and as seen in FIGS. 2 and 4, the distal part 2 is partially inserted inside the proximal part 3 in order to enable the fixation of the distal part 2 inside the proximal part 3. According to one embodiment the distal part 2 and the proximal part 3 overlap in order to be fixedly connected. According to one embodiment the distal part 2 comprises an outer extra-thickness located close to the proximal end of the distal part 8. Said extra-thickness bites or penetrates in the at least one recess 14 of the proximal part 3 for ensuring fixation of the proximal part 3 with the distal part 2.

According to one embodiment (as seen in FIG. 2), the inner diameter of the distal part 2 and of the proximal part 3 is substantially equal and constant (except for the full portion 5 and the wedge(s) 12 which protrude inside said inner diameter).

According to one embodiment, the distal part 2 comprises, before use, a constant external diameter, except for the outer extra-thickness located close to the proximal end of the distal part 8 and allowing the fixation of the distal part 2 in at least one recess 14 of the proximal part 3.

FIGS. 3 and 4 represent the bone fixation device 1 in use, upon insertion of a bone screw 100 (not shown). FIG. 5 represents the bone fixation device 1 in a vertebra 200, upon insertion of a bone screw 100.

The use of the bone fixation device 1 with a bone screw 100 as well as the advantages of the bone fixation device 1 will now be described.

The surgeon realizes a hole in the vertebra through the pedicles up to the vertebral body utilizing an appropriate drill. A bone fixation device 1 of a length corresponding to the selected bone screw length is then placed onto a mounting tool comprising preferably a guiding pin and placed securely into the drill hole by pushing, tapping, impacting or injecting until the flange 4 of the bone fixation device lies against the outer side of the vertebra. As will be apparent to those skilled in the art, the sizes of the bone fixation device 1 of the invention can vary over a broad range to meet its intended applications. After insertion of the bone fixation device 1, the bone screw 100 is inserted into the bone fixation device 1. The screw then abuts against the wedge 12 (if implemented) which is tapered towards the proximal end of the proximal part 10 and which drives the at least one pedicular wing 11 to expand and bite the vertebral pedicle. Then, after further screwing and/or inserting, the screw 100 abuts against the extra-thickness of the full portion 5 of the distal part 2 and bites inside and anchors the screw 100 inside the full portion 5. As the surgeon continues screwing, the screw 100 no longer advance with respect to the proximal part 3 (due to the flange 4 abutting against the external side of the vertebra 200 and the head of the screw 100 abutting against the proximal surface of the flange 4). Then, according to the principle of the worm drive, the screw is further screwed inside the bone fixation device 1, without longitudinal movement relative to the proximal part 3 and this rotational movement allows a proximal displacement of the full portion 5 relative to the proximal part 3. Thus the distal end of the distal part 7 moves backwards towards the proximal end 10 (it is the so-called central expansion) and the deformable area 2D is deformed or expanded. The surgeon continues screwing until the expanded or deformed deformable area 2D contacts one side of the pedicle. During such expansion phase, the proximal part 3 of the bone fixation device 1 is maintained in the same position relative to the bone by means of the flange 4. Said bone fixation device 1 ensures an efficient fixation squeezing on each side of the vertebral pedicle 201: the inner surface of the pedicle 201 is squeezed against the deformable area 2D and the outer surface of the pedicle 201 is squeezed against the flange 4. In addition, the insertion of the bone screw 100 allows the bone fixation device 1 to hook over the inner side of the pedicle thanks to the at least one pedicular wing 11 of the proximal part 3 (if implemented).

According to one embodiment, in the final anchoring position, the deformable area 2D of the bone fixation device 1 expand in the vertebral body and press on the internal side of the vertebral pedicle, while the flange 4 presses on the external side of the vertebral pedicle.

According to one embodiment, once the screw abuts against the flange 4 of the bone fixation device 1, further screwing causes the deformation of the deformable area 2D of the distal part 2 and the retraction of the distal end of the distal part 7 retracts towards the proximal end of the distal part 8.

After final expansion, as illustrated in FIG. 6, the at least three helical slots 6 abuts against each other, thereby preventing bone growth inside the bone fixation device 1.

According to an embodiment, at least one connector is mounted/joined on the screw 100, said connector is designed for allowing connection with a bridge, a rod, a plate or any means for connecting at least one medical device known to one of ordinary skill in the art to the screw. According to a preferred embodiment, said connectors are designed in order to provide an intermediate means for connecting a bridge, a rod, a plate or any means for joining at least two vertebrae to the fixation device 1 to a pedicle screw.

According to an embodiment, no blocking mechanism e.g. a bolt or a nut, is mounted/joined to the screw 100.

According to an embodiment, present invention allows a rigid connection of at least two adjacent vertebrae to one other. According to an embodiment, the linear movement of the screw 100 freely mobile into the hollow cavity does not allow central expansion.

According to one embodiment, pulling proximally the screw 100 does not allow central expansion.

According to a preferred embodiment, no external blocking means are necessary for blocking the bone fixation device 1 into an expanded state.

According to one embodiment, the insertion of the screw 100 into the bone fixation device 1 does not allow applying a compression or traction force against two vertebrae by means of which the relative position of the two adjacent vertebral bodies can be varied relative to one another.

Thus the anchorage of the bone fixation device 1 (as seen in FIGS. 3, 4 and 5) is efficiently performed due to:
  the at least one pedicular wing 11 (if implemented) which
    bites inside the inner surface of the pedicle of the patient, prevents rotation of the bone fixation device 1 and ensures fixation with respect to the vertebra; and/or the at least three helical slots 6, which enable the central expansion, and the flange; said two parts enable:
  to expand the bone fixation device 1 in the vertebral body and to anchor it with respect to the vertebral body; and
  to squeeze the pedicle between on one side the flange and on the other side the expanded deformable area and to ensure an optimal anchorage with respect to the pedicle and to the vertebra of the patient.

The at least three helical slots 6 further allow, during expansion, that the at least three helical slots 6 disappear as each lateral side of the at least three helical slots 6 abuts against each other. Thus the distal part 2 of the bone fixation device 1 which is located, in use, inside the vertebral body, does not present hollows or asperities, or at least minimizes the hollows and asperities.

According to the applicant knowledge the slots in helical form before use are particularly advantageous and have not been used, for the present applications, in the prior art.

According to one embodiment, the removal of the bone fixation device 1 is facilitate as the at least one pedicular wing 11 expands towards the distal part 2. When pulling out the bone fixation device 1, the at least one pedicular wing 11 will be closed easily. Moreover, the lateral sides of the at least three helical slots 6 are contiguous in use, thus facilitating the removal as no or few bone has grown inside the distal part.

Figure 8:
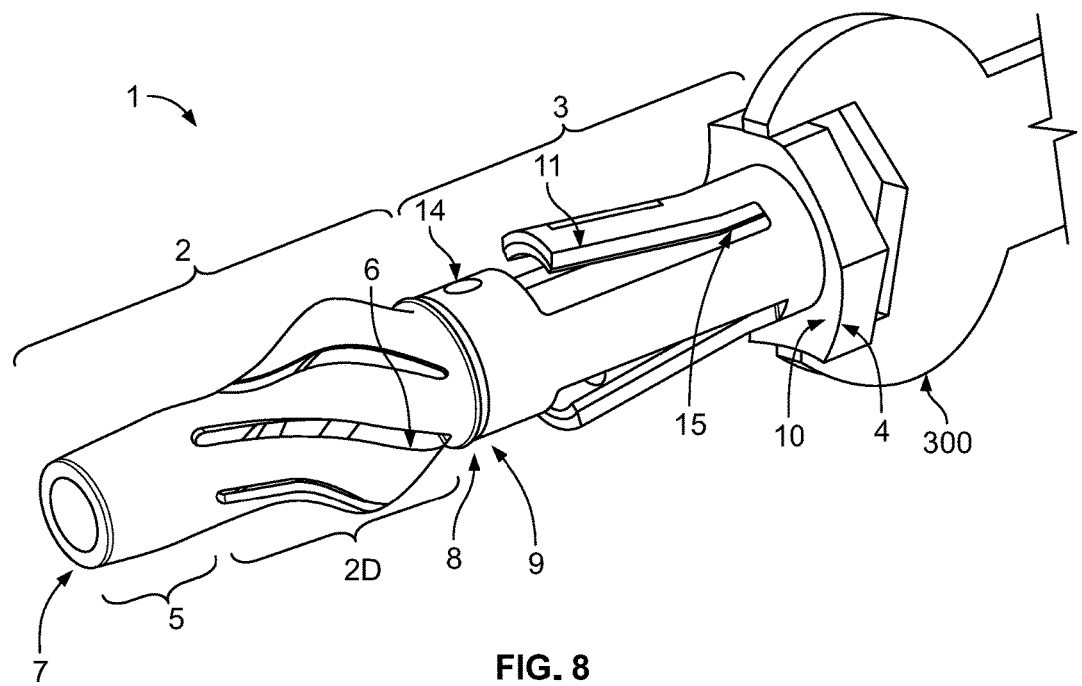
FIG. 8 represents the perspective view of FIG. 3 with an engaging tool secured thereon.

According to one embodiment, the bone fixation device 1 may be removed using any driving tool that one skilled in the art would find suitable such as, for example, a screwdriver, wrench, or screw extractor. One example of a wrench 300 is shown in FIG. 8, the wrench 300 secured to the bone fixation device 1.

According to one embodiment, prior to remove the bone fixation device 1, the screw 100 inserted into the bone fixation device 1 is removed by unscrewing.

According to one embodiment, the screw 100 and the bone fixation device 1 are removed independently, preferably in two independent steps: first, the screw is unscrewed and removed from the bone fixation device 1; and then the fixation bone device 1 is removed from the bone.

According to a preferred embodiment, the screw 100 is removed from the bone fixation device 1 by unscrewing without applying a longitudinal force against the screw 100.

According to one embodiment, in use, the at least three contiguous helical slots 6 isolates the internal volume of the bone fixation device 1 from bone growth. Thus after removal of the screw 100, due to the flexibility of the deformable part 2D, the bone fixation device 1 may be removed by pulling.

According to another embodiment, the at least three helical slots 6 are first unexpanded, then the screw 100 is removed and then the unexpanded bone fixation device 1 is removed. According to said embodiment, the at least three helical slot 6 (i.e. the deformable area 2D) is unexpanded by unscrewing and simultaneously applying a pushing force against the head of the screw 100. The force applied against the screw 100 blocks the proximal linear displacement of the screw 100 and then converts the rotational movement of the screw in a distal linear movement of the full portion 5 with respect to the screw 100. This distal movement of the full portion 5 causes the distal end of the distal part 7 to draw away from the proximal end of the distal part 8 and then un-expansion of the bone fixation device 1.

According to an embodiment, the linear movement of the screw 100 freely mobile into the hollow cavity does not allow the at least three helical slots 6 to returning to their non-expanded position, more generally does not allow to un-expand the bone fixation device 1.

According to one embodiment, the full portion 5 is not compatible with a threaded actuator wherein the thread of the distal part of the actuator is threadably un-connected to the full portion 5 only for unlocking the anchor device 1 into a free-to-moving state, throughout the hollow cavity.

According to one embodiment, pushing the screw 100 does not allow central un-expansion.

The present invention also relates to the use of the bone fixation device 1 according to the present invention with a bone screw 100. The present invention also relates to a kit of parts for improving the holding strength and purchase of a screw used for the treatment of spinal disorders comprising:
  at least one bone fixation device 1 according to the present invention; and
  at least one bone screw designed to be used with said at least one bone fixation device 1.

According to one embodiment, said kit of parts further comprises:
  a tool for mounting and/or removing the bone fixation device 1, wherein the tool is adapted to the shape of the flange 4; and
  a guiding pin adapted to pass through the hollow cavity of the bone fixation device 1 and optionally to expand the at least one pedicular wing 11 of the bone fixation device 1 upon insertion.

The invention claimed is:

1. A bone fixation device for securing attachment between a screw and a vertebra comprising two pedicles, comprising a hollow cavity having a longitudinal axis, a distal part having itself a distal end and a proximal end, a proximal part having itself a distal end and a proximal end and a flange at the proximal end wherein:
  the distal part comprises a uniform outer diameter in a non-expanded position along with a deformable area having at least three helical slots that are helical in the non-expanded position; and
  the distal part comprises a full portion located distally after said at least three helical slots, the full portion including a thickness that is thicker than a thickness throughout a length of a remainder of the distal part;
and wherein said full portion cooperates with the screw such that once the screw abuts against the flange of the bone fixation device, further screwing causes the deformation of the deformable area of the distal part and the retraction of the distal end of the distal part towards the proximal end of the distal part; and in that after screwing, borders of each of the at least three helical slots abut against each other.

2. The bone fixation device according to claim 1, wherein said deformation of the distal part is designed to allow the deformable area of the bone fixation device to expand in the vertebral body and to press on the internal side of the vertebral pedicle, while the flange presses on the external side of the vertebral pedicle.

3. The bone fixation device according to claim 1, wherein said full portion comprises an inner thread.

4. The bone fixation device according to claim 1, wherein said proximal part further comprises at least one pedicular wing.

5. The bone fixation device according to claim 4, wherein a wedge tapered towards the proximal end of the proximal part is located under each of said at least one pedicular wing.

6. The bone fixation device according to claim 4, wherein said at least one wing is arranged to expand upon insertion of a mounting tool or a screw.

7. The bone fixation device according to claim 1, wherein said proximal part is made of a biocompatible metal, alloy or polymer and the distal part is made of a biocompatible polymer.

8. The bone fixation device according to claim 1, wherein said proximal part further comprises at least one slot for receiving an inner proximal part made of a soft material, adapted to cover the inner surface of the proximal part.

9. The bone fixation device according to claim 1, wherein said at least three helical slots are wrapped around the distal part in the direction of the longitudinal axis.

10. The bone fixation device according to claim 1, wherein said at least three helical slots have a lead from 0.05 millimeter to 100 millimeters.

11. The bone fixation device according to claim 1, wherein said at least three helical slots have a width from 0 to 1 centimeter.

12. The bone fixation device according to claim 1, wherein said distal part comprises 3, 4, 5, 6, 7, 8, 9 or 10 helical slots wrapped around the distal part.

13. The bone fixation device according to claim 1, wherein the full portion includes an inner diameter that is smaller than an inner diameter of the rest of the distal part such that the screw intended to be inserted inside the bone fixation device does not interact with the distal part except in the full portion.

14. A kit of parts for improving the holding strength and purchase of a screw used for the treatment of spinal disorders comprising:
at least one bone fixation device according to claim 1; and
at least one bone screw designed to be used with said at least one bone fixation device.

15. A kit of parts according to claim 14 further comprising:
a tool for mounting and/or removing the bone fixation device, wherein the tool is adapted to the shape of the flange; and
a guiding pin adapted to pass through the hollow cavity of the bone fixation device and optionally to expand the at least one pedicular wing upon insertion.

16. A bone fixation device for securing attachment between a screw and a vertebra comprising two pedicles, comprising a hollow cavity having a longitudinal axis, a distal part having itself a distal end and a proximal end, a proximal part having itself a distal end and a proximal end and a flange at the proximal end wherein:
the proximal part includes at least one arm extending from the proximal end of the proximal part to a free end, wherein in a first position, the at least one arm is located at a substantially similar distance from the longitudinal axis at the proximal end of the proximal part and at the free end, and wherein in a second position, the at least one arm varies in distance from the longitudinal axis between the proximal end of the proximal part and the free end;
the distal part comprises a substantially uniform outer diameter in a non-expanded position along with a deformable area having at least three helical slots that are helical in the non-expanded position; and
the distal part comprises a full portion located distally after said at least three helical slots;
and wherein said full portion cooperates with the screw such that once the screw abuts against the flange of the bone fixation device, further screwing causes the deformation of the deformable area of the distal part and the retraction of the distal end of the distal part towards the proximal end of the distal part; and in that after screwing, borders of each of the at least three helical slots abut against each other.

17. The bone fixation device according to claim 16, wherein the at least one arm is helical.

18. The bone fixation device according to claim 16, wherein the at least one arm includes a wedge facing the longitudinal axis, the wedge tapered towards the proximal end of the proximal part.

19. The bone fixation device according to claim 16, wherein the at least one arm includes an outer surface that is at least one of ribbed, threaded, and fretted.

20. The bone fixation device according to claim 16, wherein said proximal part is made of a biocompatible metal, an alloy or a polymer and the distal part is made of a biocompatible polymer.

* * * * *

UNITED STATES PATENT AND TRADEMARK OFFICE
CERTIFICATE OF CORRECTION

| | | |
|---|---|---|
| PATENT NO. | : 10,405,890 B2 | Page 1 of 1 |
| APPLICATION NO. | : 15/021640 | |
| DATED | : September 10, 2019 | |
| INVENTOR(S) | : Yves-Alain Ratron et al. | |

It is certified that error appears in the above-identified patent and that said Letters Patent is hereby corrected as shown below:

On the Title Page

Item (72):
Please replace "Jean-Francois" with --Jean-François--

In the Claims

In Column 22, Line 8:
Please replace "substantially similar" with --similar--

In Column 22, Line 14:
Please replace "substantially uniform" with --uniform--

Signed and Sealed this
Twenty-sixth Day of May, 2020

Andrei Iancu
*Director of the United States Patent and Trademark Office*